US007240251B2

(12) United States Patent
Popescu

(10) Patent No.: US 7,240,251 B2
(45) Date of Patent: Jul. 3, 2007

(54) METHOD AND SYSTEM FOR DATA TRANSMISSION IN A CT DEVICE, WITH INTEGRATED ERROR MONITORING AND DIAGNOSIS

(75) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 496 days.

(21) Appl. No.: 10/846,257

(22) Filed: May 14, 2004

(65) Prior Publication Data
US 2005/0005206 A1 Jan. 6, 2005

(30) Foreign Application Priority Data
May 16, 2003 (DE) ................................ 103 22 138

(51) Int. Cl.
*H04L 1/24* (2006.01)
*A61B 6/03* (2006.01)
(52) U.S. Cl. ........................ 714/704; 714/37; 714/712; 378/21
(58) Field of Classification Search .. 714/37; H04L 1/24
See application file for complete search history.

(56) References Cited

U.S. PATENT DOCUMENTS

| 4,259,584 | A |   | 3/1981  | Krumme |
|-----------|---|---|---------|--------|
| 5,140,696 | A |   | 8/1992  | Fox |
| 5,535,033 | A |   | 7/1996  | Guempelein et al. |
| 6,105,149 | A | * | 8/2000  | Bonissone et al. ............ 714/26 |
| 6,501,821 | B2|   | 12/2002 | Betz |
| 2002/0150045 | A1 |   | 10/2002 | Vogtmeier et al. |
| 2003/0149921 | A1 | * | 8/2003 | Lau et al. ................... 714/704 |
| 2003/0185427 | A1 | * | 10/2003 | Hsieh et al. ................. 382/131 |

(Continued)

FOREIGN PATENT DOCUMENTS

DE     10140037 A1 * 2/2003

(Continued)

OTHER PUBLICATIONS

"Beyond Bit Error Ration—Gain New Insight From Studying error Distributions," Foster et al. Agilent Technologies Technical Paper, Literature No. 5988-8037EN, Sep. 26, 2002.

(Continued)

*Primary Examiner*—R. Stephen Dildine
(74) *Attorney, Agent, or Firm*—Schiff Hardin LLP

(57) ABSTRACT

In a system and an associated method, for data transmission in a computed tomography device, having a data acquisition unit in which measurement data are acquired, converted into a bit stream, and communicated to a transmitter apparatus on a rotating part of the computed tomography device, wherein the transmitter transmits the bit stream to a stationary part of the computed tomography device, and having a receiver apparatus on the stationary part that receives the bit stream from the transmitter apparatus and communicates it to an image reconstruction unit that further processes the bit stream communicated by the receiver apparatus for the reconstruction of the image, the transmitter apparatus and the receiver apparatus each have an error recognition module that monitors the bit stream for errors and signals recognized errors to an error processor that determines the number and rate and/or duration of the recognized errors and stores these in a log data file for an evaluation. Errors thus can be recognized in real time and can be used for error diagnosis without the use of an additional testing tool.

28 Claims, 5 Drawing Sheets

U.S. PATENT DOCUMENTS

| | | | |
|---|---|---|---|
| 2004/0249575 A1* | 12/2004 | Hellmold | 702/19 |
| 2005/0022085 A1* | 1/2005 | Vo et al. | 714/738 |
| 2005/0209790 A1* | 9/2005 | Niethammer | 702/28 |
| 2006/0200708 A1* | 9/2006 | Gentieu et al. | 714/704 |

FOREIGN PATENT DOCUMENTS

| | | | |
|---|---|---|---|
| DE | 10164643 A1 * | 7/2003 | |
| EP | 305036 A2 * | 3/1989 | |
| EP | 0 981 994 | 3/2000 | |
| EP | 1 058 191 | 12/2000 | |

OTHER PUBLICATIONS

An Introduction to Error Location Analysis—Are all your errors truly random? Agilent Technologies Application Note 1550-2, Literature No. 5980-0648E, Apr. 2000.

* cited by examiner

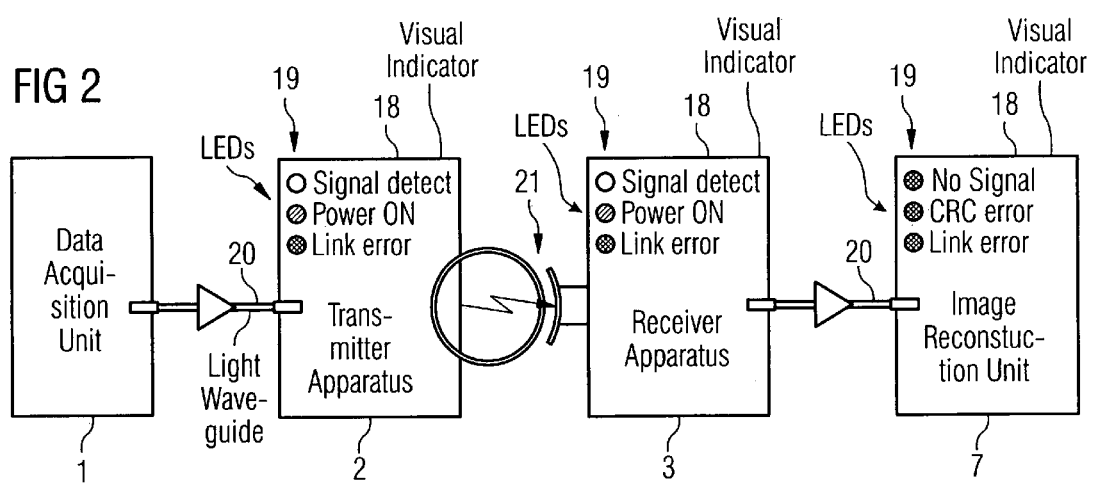
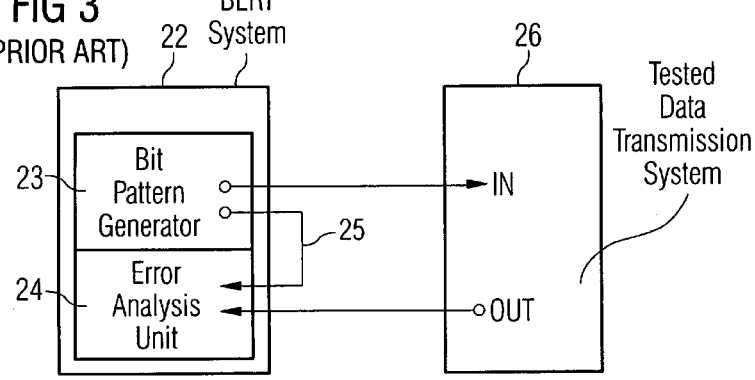

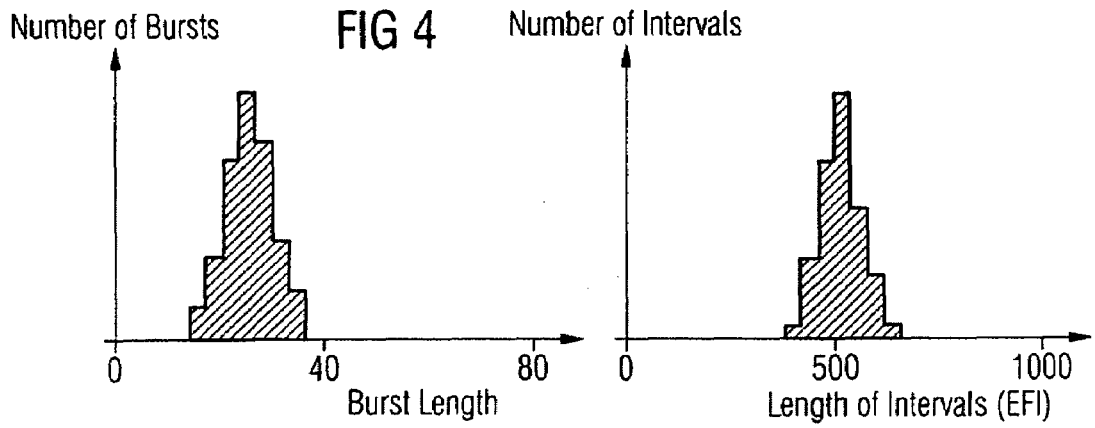
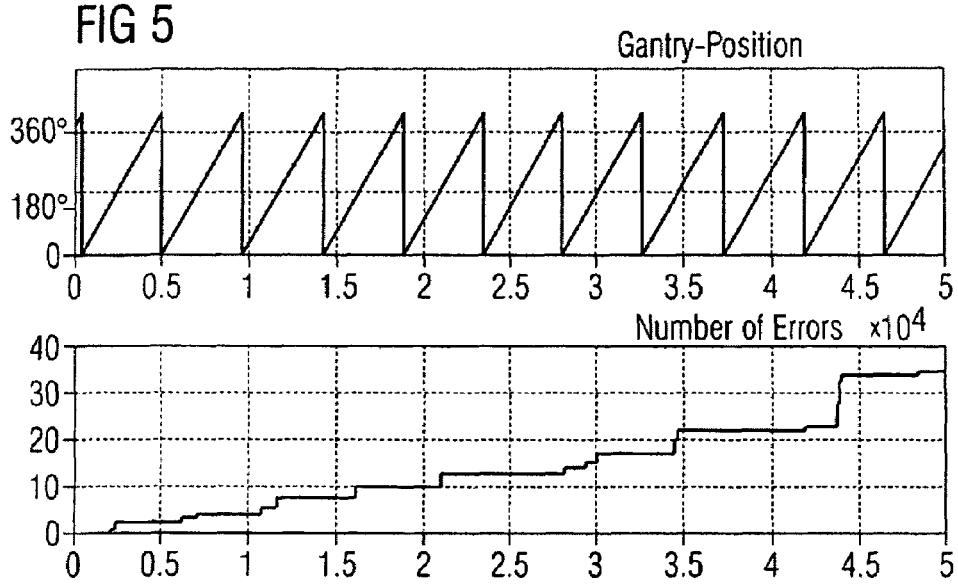
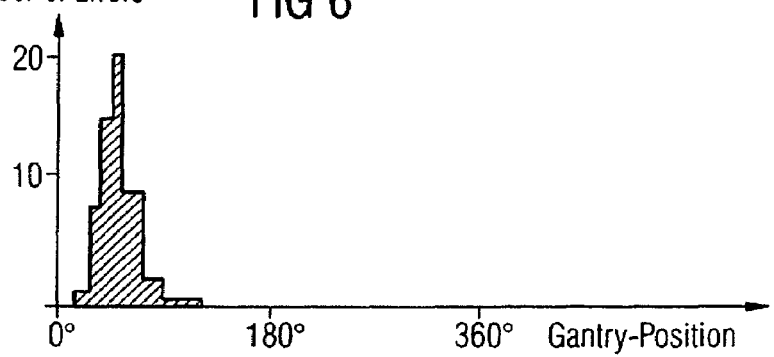

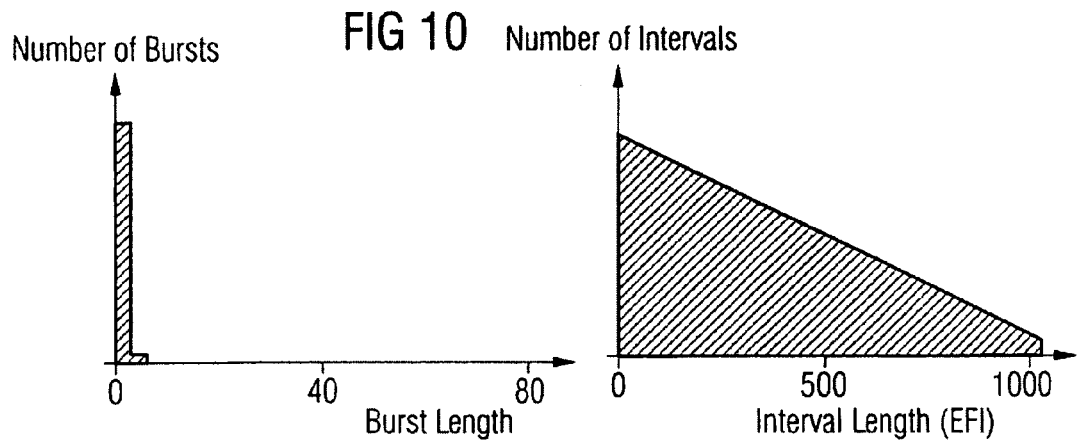
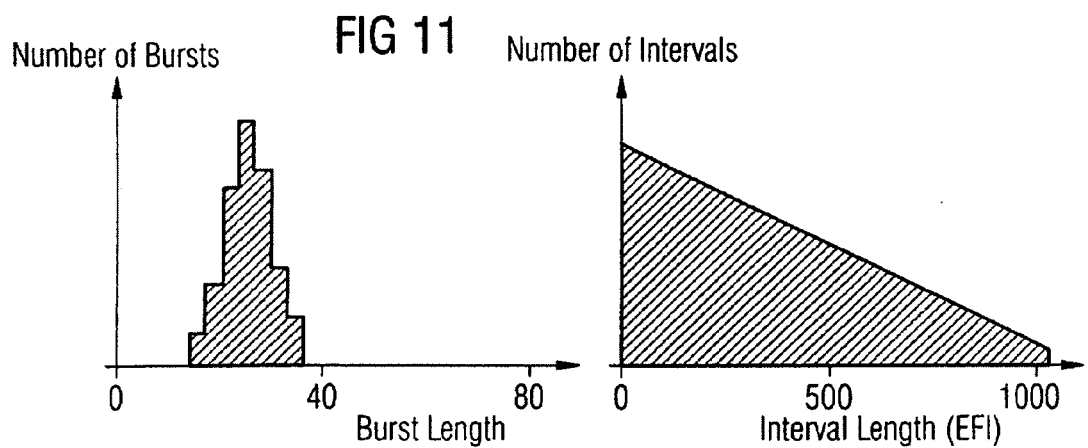

METHOD AND SYSTEM FOR DATA TRANSMISSION IN A CT DEVICE, WITH INTEGRATED ERROR MONITORING AND DIAGNOSIS

BACKGROUND OF THE INVENTION

1. Field of the Invention

The present invention relates to a data transmission system, as well as a method for monitoring data transmission in a computed tomography (CT) device or in an X-ray device that can be used for tomography, having a data acquisition unit in which measurement data are acquired, converted into a bit stream, and communicated to a transmitter apparatus on a rotating part of the computed tomography apparatus or the X-ray device, the transmitter then transmitting the bit stream to a stationary part of the computed tomography apparatus or of the X-ray device, and having a receiver device on the stationary part that receives the bit stream from the transmitter apparatus and communicates it to an image reconstruction unit that further processes the bit stream communicated by the receiver device for image reconstruction.

2. Description of the Prior Art

In medical imaging technology, computed tomography apparatus often are used in which a very large amount of measurement data is simultaneously acquired, communicated to an image reconstruction unit, and further processed in order to reconstruct the desired images. The data transmission system required for this must be capable of high-speed transmission, due to the large amount of measurement data that occurs per time unit, and must also ensure a maximally error-free transmission between the rotating part of the computed tomography apparatus (the gantry) and the stationary part. Similar requirements exist in the case of C-arm X-ray devices. Such X-ray devices, or other X-ray devices capable of tomography, are subsumed under the term "computed tomography device" below.

Various technologies are known for the data transmission between the rotating part and the stationary part.

The known technologies can be divided into transmission technologies using capacitive coupling and those using optical coupling. In transmission using capacitive coupling, the signals are transmitted from a transmitter fastened to the rotating part to an antenna situated on the stationary part. Thus, German OS 100 07 601 specifies an apparatus for data transmission in which a waveguide is used as a transmitter. For the data transmission, the data are modulated onto a carrier signal and are coupled into the waveguide. An antenna situated in a particular geometrical fashion relative to the waveguide receives the carrier signal in contactless fashion, so that after demodulation of the carrier signal the data are available at the stationary part. In the application depicted in this publication, the waveguide is fastened along the periphery of the C-arm of a C-arm X-ray device, and the antenna is fastened to the mount of this C-arm.

U.S. Pat. No. 5,140,696 specifies an apparatus for signal transmission between elements that are moved relative to one another, in particular in a computed tomography apparatus, in which as a transmitter a circular strip conductor is situated on the periphery of the gantry, and as a receiver a short segment of a strip conductor is provided on the stationary part in the immediate vicinity of the transmission line. The data transmission takes place in the same manner as in the reference cited above.

In signal transmission using optical coupling, the transmission of the data takes place via an optical interface. Thus, U.S. Pat. No. 4,259,584 specifies an apparatus for signal transmission, in particular for a computed tomography apparatus, in which on the stationary part there is fashioned a ring that runs around the rotational center and is made of an optical waveguide at the output point of which there is situated a demodulator. On the rotating part, opposite the optical waveguide a light source is fastened, the intensity of which is modulated with the data that are to be transmitted. The modulated light signals are constantly coupled into the optical waveguide ring during the relative movement due to this geometrical arrangement, and are received by the demodulator, which extracts the data by demodulation.

U.S. Pat. No. 5,535,033 discloses a signal transmission apparatus in which a ring made of an optically conductive material is fastened on the rotating part of a computed tomography apparatus as a part of a transmission apparatus that also radiates the coupled-in light perpendicular to its longitudinal axis. The data to be transmitted are coupled into this ring by modulation of a light source, and are received at the stationary part via an optoelectrical detector. Due to the annular construction of the transmitter apparatus, here as well reception of the data by the receiver is possible during almost every phase of rotation.

Independent of the data transmission technology used, a computed tomography device has a data acquisition unit that converts the measurement data obtained from the multiplicity of detector channels into a bit stream, which generally is serial, and communicates this bit stream to a transmitter device on the gantry. The transmitter device transmits the serial bit stream to a receiver device on the stationary part of the computed tomography device, which in turn forwards this bit stream to the image reconstruction unit, in which the bit stream generally is first again demultiplexed and subsequently further processed for image reconstruction. This data connection between the data acquisition unit and the image reconstruction unit is relatively complex due to the numerous components involved, so that transmission errors that may occur can be diagnosed only with difficulty. This is true both for the design and integration phase and for the manufacturing phase of the system; in each of these phases it is difficult to test the quality of the data connection and to identify determinate points in the data transmission chain. Additionally, when data transmission errors occur in the clinical environment it is very difficult and time-intensive, and thus expensive, for service personnel to discover the faulty components in the data chain. In computed tomography devices, the testing of data transmission is made more difficult by the fact that during the operation of the computed tomography device the gantry rotates continuously, so that it is almost impossible to couple test devices to the data acquisition unit as a source of data.

In order to test the quality of data connections, from communication technology the acquisition and evaluation of the bit error rate (BER) is known, which indicates the number of bits transmitted with errors in relation to all the bits communicated in a predetermined interval. For testing data transmission systems, special measurement devices are available for determination of the bit error rate; these devices are known as BERT (Bit Error Rate Tester) systems. These test systems contain a bit pattern generator that sends a predefined bit sequence via the data transmission system, and an error analysis unit that analyzes the transmitted bit sequence. A reference clock pulse is transmitted via a direct connection between the bit pattern generator and the error analysis unit in order to correctly read out the obtained bit sequence. FIG. 3 shows, as an example, such a test system 22, with a bit pattern generator 23 and an error analysis unit 24, for testing a data transmission system 26. The error analysis unit 24 enables the acquisition of the number of errors during the data transmission, the classification of the errors, and the determination of the position of the errored bit within the data stream, so that from these data conclusions can be made concerning the cause of the errors. Examples of such an error analysis can be found in the following publications: G. M. Foster and T. Waschura, "Beyond Bit Error Ratio B Gain New Insight from Studying Error Distributions," Agilent Technologies Technical Paper, Literature No. 5988-8037EN, Sep. 26, 2002, 8 2002 Agilent Technologies, http://literature.agilent.com/litweb/pdf/5988-8037EN.pdf, and "An Introduction to Error Location Analysis B Are All Your Errors Truly Random?," Agilent Technologies Application Note 1550-2, Literature No. 5980-0648E, April 2000.

Such a known test system cannot be used in computed tomography devices, because the data acquisition unit as a data source and the image reconstruction unit as a data receiver are continuously rotating relative to one another. Most available test systems contain the bit pattern generator and the error analysis unit in the same housing, so that a physical separation of them is not possible. Even if the bit pattern generator were provided separately, it would be practically impossible to fasten it to the rotating gantry, due to the small space available and the resulting disturbance to the mechanical equilibrium. In addition, in a computed tomography device there is only one high-speed connection between the rotating part and the stationary part, so that no separate connection is available for the communication of the reference clock pulse. A further problem is presented by the complex transmission chain in a computed tomography device, in which first a parallel data stream is converted into a serial bit stream, the data are coded in order to integrate the clock signal into the data stream, the serial bit stream is transmitted between a continuously rotating part and the stationary part, the contained clock signal is extracted in order to sample the data using the extracted clock signal, and finally the serial data stream is converted back into parallel words. For the testing of such a transmission chain, parallel test systems are necessary, requiring a very expensive and complex interface to the test system.

For this reason, heretofore service personnel in the clinical environment have approached the problem of finding the cause of data transmission errors in computed tomography devices simply by successively exchanging individual components. This trial and error technique is very time-intensive and expensive, because all parts that can be exchanged must be kept available. In addition, this technique is useless in the case of causes of error that occur from an outside source, for example errors that occur due to interference between external sources of disturbance and the transmission between the transmitter apparatus and the receiver apparatus of the computed tomography device.

SUMMARY OF THE INVENTION

This object is achieved in accordance with the invention by a data transmission system for data transmission in a computed tomography device having, in a known manner, a data acquisition unit in which measurement data are acquired, converted into a bit stream, and communicated to a transmitter apparatus, situated on the rotating part of the computed tomography device, that transmits the bit stream to the stationary part of the computed tomography device, and a receiver apparatus on the stationary part, which receives the bit stream from the transmitter apparatus and communicates it to the image reconstruction unit, which further processes the bit stream communicated from the receiver apparatus for the reconstruction of the image. In the inventive data transmission system, at least the transmitter apparatus and the receiver apparatus each have an error recognition module that monitors the bit stream for errors and signals known errors to an error processor that determines the number and duration, or the number and rate, or the number, duration, and rate, of the recognized errors and stores them in a log data file for an evaluation. This monitoring for errors takes place in real time during the normal operation of the computed tomography device, so that at all times the current state of the data transmission chain can be checked by looking into the log data file. In one embodiment of the inventive data transmission system, as well as the associated method, a warning message is generated when predeterminable thresholds are exceeded for the error rate, the number of errors, and/or the duration of the errors. Preferably, the image reconstruction unit also contains such an error recognition module, and stores recognized errors, with the number, rate, and/or duration thereof, in the log file.

Due to the separate acquisition of errors in the bit stream at the various points of the data transmission chain, when errors occur it can be recognized at all times in which transmission branch the errors have occurred. This makes it considerably easier for the service personnel to locate the cause of the error. Through the provision of a remote access to the log file, for example via a closed network or the Internet, in this way it is also possible to make a remote diagnosis, or it can be made possible for the service personnel to prepare, before traveling to the site, the specific additional tests that are to be performed.

In the preferred embodiment of the data transmission system and the associated method, the error recognition is based on the checking of CRC codes that are transmitted with the data in the bit stream. These CRC codes represent signatures of the associated data words, so that a transmission error can be recognized by a deviant signature. In a further embodiment, alternatively or additionally the clock pulse signal is recovered from the bit stream. If this is not possible, this represents an error. Finally, in addition the signal strength of the bit stream can be checked for sufficient strength level.

In a preferred embodiment of the inventive data transmission system, the data acquisition unit contains a bit pattern generator that generates, in response to an input by the service personnel, selectable predetermined or predeterminable bit patterns that are converted in the data acquisition unit into a serial bit stream and are communicated to the image reconstruction unit in the same manner as the measurement data. In this way, with the aid of an error analysis module integrated into the image reconstruction unit the service personnel can carry out specific tests in order to find the causes of the errors. The bit patterns produced in this way, as well as the evaluation steps that can be carried out, are known from the prior art cited above, and also can be used here in the same manner. However, the inventive data transmission system, and the associated method, do not require the use of an external test system, so that the problems that otherwise occur are avoided. In the preferred embodiment, the error analysis unit determines the bit error rates, in order to carry out additional evaluation steps when a predeterminable threshold for these bit error rates is exceeded. The error analysis module can be designed for the detection of systematic bit and burst errors, for the detection of random bit and burst errors, or for error correlation analysis for the detection of position-related or pattern-related errors.

In a further embodiment of the inventive data transmission system, a visual indicator with which the recognition of an error is indicated, is allocated to each error recognition module. Thus, such a visual indicator, for example in the form of one or more light-emitting diodes, can be situated in the area of the respective error recognition module, i.e., in the area of the transmitter apparatus, in the area of the receiver apparatus, or, if warranted, in the area of the image reconstruction unit on the computed tomography device, these diodes being correspondingly illuminated when errors occur. Due to this location of the visual indicator, it becomes immediately visible in which transmission branches errors have occurred. Of course, such a visual indication also can be made on the monitor of the user of the computed tomography device.

DESCRIPTION OF THE DRAWINGS

FIG. 2 shows an example of visual display units within the transmission chain of the inventive data transmission system.

FIG. 3 shows an example of a known BERT system.

FIG. 4 is an example of histograms based on the recognized errors.

FIG. 5 shows an example of the occurrence of errors in correlation with the position of the gantry.

FIG. 6 is an example of a histogram that indicates errors in correlation with the gantry position.

FIG. 10 is an example of histograms of the distribution of the burst length, as well as of the error-free intervals.

FIG. 11 is a further example of histograms of the distribution of the burst length, as well as of the number of error-free intervals.

DESCRIPTION OF THE PREFERRED EMBODIMENTS

In the following example, reference is made to a data transmission system of a computed tomography apparatus, in which the transmission between the rotating part and the stationary part takes place via a high-frequency connection, by means of a slip ring that forms a transmission antenna. Of course, this is only one specific construction of such a data transmission system. The present invention also can be applied to many other transmission technologies between the rotating part and the stationary part, such as for example optical transmission technologies, or non-contactless transmission technologies, as well as those having a multiplicity of parallel or segmented slip rings.

Figure 1:
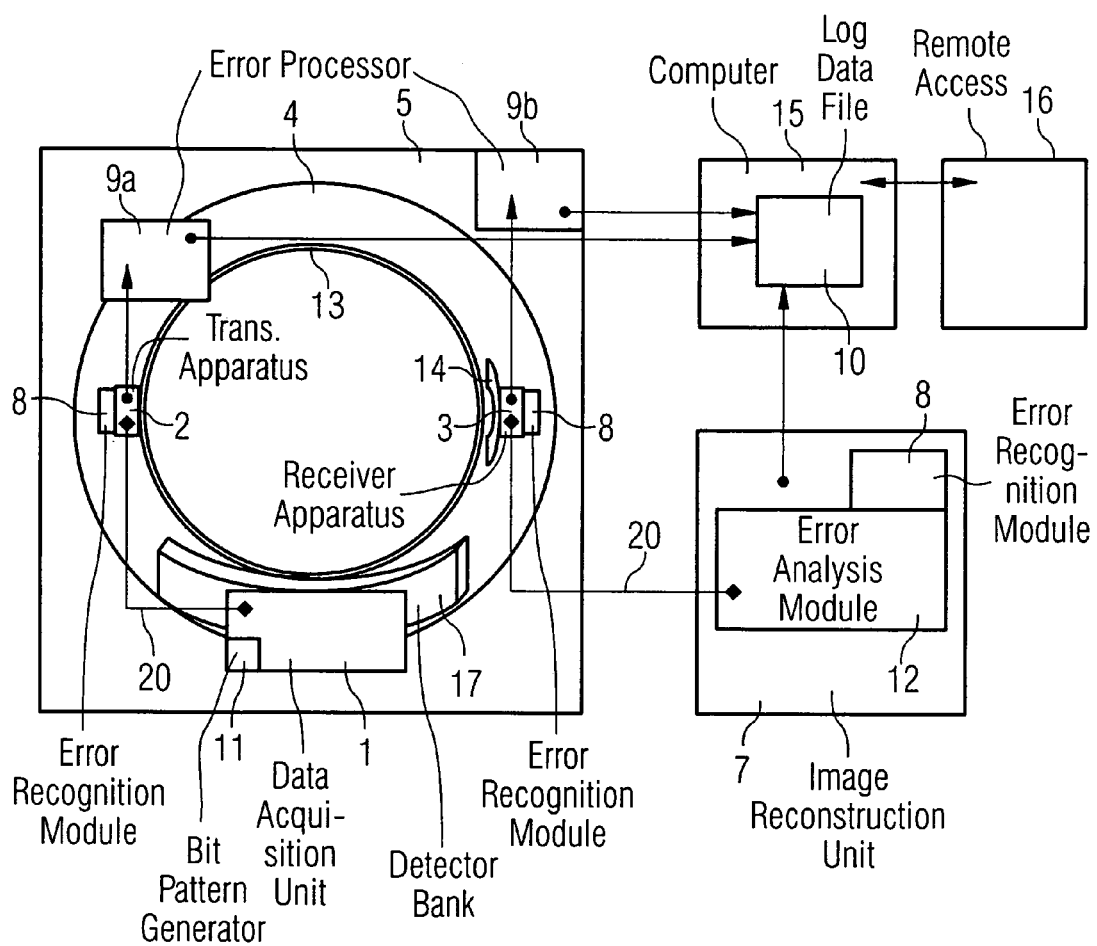
FIG. 1 is a block diagram an example of the inventive data transmission system.

FIG. 1 shows, in a highly schematic view, a part of a computed tomography apparatus with a stationary part 5 as well as gantry 4 that rotates in the stationary part, on which there are situated the X-ray tube (not shown) and a detector bank 17 situated opposite the X-ray tube. The voltage signals obtained by the individual detector channels of the detector bank 17 are converted into a serial bit stream by a data acquisition unit 1, using a parallel/serial converter, and, using an electro-optical converter, and are communicated to a transmitter apparatus 2 as an optical bit stream via an optical waveguide 20. Transmitter apparatus 2 has an opto-electrical converter and a radio-frequency output, via which the serial bit stream is fed, as a radio-frequency signal, into a transmission ring 13 with an integrated transmission antenna. The radio-frequency signals of the rotating gantry 4 are received by a receive apparatus 3, which is fastened to the stationary part 5, by a receive antenna 14, and are converted into an optical bit stream by an electro-optical converter, and are transmitted to an image reconstruction unit 7 via an optical waveguide 20. The image reconstruction unit 7 has an optoelectrical converter as well as a serial/parallel converter for converting the obtained serial data into parallel data, which are further processed in a known manner for the image reconstruction.

In the inventive data transmission system, in the present example a bit pattern generator 11 is additionally integrated into data acquisition unit 1. By the implementation of this bit pattern generator 11 into data acquisition unit 1, the use of an external test system is avoided. The present bit pattern generator 11 is thus available at all times to the testing personnel at the location of the computed tomography apparatus. Another advantage of this integrated generator is that, using it, the parallel/serial, serial/parallel, and parallel segments of the data connection can be tested directly. The bit pattern generator is configured and started by the service personnel using a software program that runs on the image reconstruction unit, in order to produce a selectable predetermined or predeterminable test bit pattern. This test bit pattern is converted into a serial bit stream in the data acquisition unit 1, and is transmitted to the image reconstruction unit 7 via the transmission chain. There it is stored in a storage unit, as are the measurement data during the normal operation of the computed tomography apparatus. The image reconstruction unit 7 has an error analysis module 12 in the form of a software module that evaluates the obtained or stored data in a known manner, in order to make, by determining the bit error rate, a quantitative prediction concerning the quality of the data connection in different operating modes of the computed tomography apparatus. If the determined bit error rates lie above predeterminable thresholds, the obtained bit patterns are evaluated for the classification of the errors in a known manner. In the following exemplary embodiments, examples of the evaluation of this received bit pattern are examined in more detail. The result of the evaluation is communicated to the user via the available interface to the computer 15.

In the inventive data transmission system, the serial bit stream, as well as the signal strength, is monitored along the data connection in real-time during normal operation, and errors that occur are stored, with respect to their number and duration, in a log data file 10 in the computer 15. The log data file can be queried via a remote access 16, for example via the Internet, by service personnel, so that already before a service visit the service center contains a considerable amount of information concerning the location of the error and replacement parts that may be required. For this error monitoring in real time, transmitter apparatus 2, the receive apparatus 3, and the image reconstruction unit 7 each contain an error recognition module 8 that checks the received bit streams for errors. This takes place on the basis of the CRC code that was added to the data in the serial bit stream by the data acquisition unit. Generally, this CRC code is checked for correctness in the image reconstruction unit 7. In the case of deviations, the respective data packet is marked as an erroneous data packet. The number of erroneous packets in relation to the overall number of packets transmitted can be used as a measure of the quality of the data connection. If the number of erroneous data packets exceeds a predeterminable value, a warning message is produced. In the same way, error recognition modules 8 of transmission apparatus 2 and of receive apparatus 3 monitor the serial bit stream and report errors to error processor 9a, situated on rotating part 4, or to error processor 9b, situated on stationary part 5. These error processors 9a or 9b count the number of errors, as well as the respective duration of the errors. If these values exceed or fall below predeterminable limits, warning messages are likewise produced. The number of errors, as well as their duration, is stored in log data file 10 by error processors 9a, 9b. Besides the error recognition, error modules 8 also acquire the signal strength of the incoming optical signal in the case of transmitter apparatus 2, and the signal strength of the incoming radio-frequency signal in the case of receive apparatus 3, as well as the strength of the incoming optical signal in the case of image reconstruction unit 7. In addition, other parameters, such as the possibility of recovering the clock signal contained in the serial data stream, can of course also be tested.

FIG. 2 shows a highly schematized view of a construction of the present data transmission system, in which visual indicator units 18 are used for the status of the respective error recognition modules 8. The serial bit stream generated by data acquisition unit 1 is communicated via optical waveguide 20 to transmitter device 2, in which the error recognition module monitors the serial bit stream for signal strength and errors. The visual indicator unit 18, having a number of light-emitting diodes 19, is connected to this transmitter apparatus 2, and indicates sufficient signal strength, the availability of the power supply, and errors that may occur. In the same way, such a visual indicator unit 18 is attached to receive apparatus 3, and correspondingly monitors the serial bit stream received via RF connection 21. The same holds for visual indicator units 18 on image reconstruction unit 7, as can be seen in the Figure. Through this arrangement of visual indicator units 18, the error state can be seen immediately, without intervention in the system. This saves time for the test personnel, and for certain rough errors avoids the necessity of having to carry out a complete test sequence.

The error analysis module 12 of the image reconstruction unit is realized as a software module that analyzes, according to particular specifications, the data obtained from image reconstruction unit 7 or called from log data file 10 and in particular locates and classifies the errors within the serial bit stream. The bit errors in the data connection of a computed tomography apparatus can originate from various error sources. The knowledge of the sources of error is important in order to enable controlling of the service activities. Thus, for example, it is important to distinguish whether the error is caused by a defective component of the data connection, or by increased interference with a source of disturbance located outside or inside the CT system.

FIG. 4 shows an example of an evaluation of the error data obtained from the log data file, or of the errors obtained through the evaluation of a transmitted predetermined bit pattern. In this example, the source of an asynchronous interference is located that is situated outside the data connection itself, but within the computed tomography apparatus. The radio-frequency connection between the transmitter apparatus and the receiver apparatus is very sensitive to interference between the RF generator and the rotating motor or the high-power frequency inverter that drives this motor. In order to identify this interference, the two histograms shown in FIG. 4 are produced, which represent the distribution of the error burst length, as well as the distribution of the error-free intervals. From these histograms it can be seen whether an asynchronous interference having a systematic repetition rate and repetition duration is present. In correlation With the data rate and the error rate, the frequency of the asynchronous interference is calculated. This provides a first indication of the source of the interference. Subsequently, the service personnel can determine through countertests whether this indication is correct.

FIG. 5 shows a further example of the evaluation of the obtained error data. In computed tomography devices, geometrical deviations of the RF antenna due to tolerances produce errors that often occur at the same angular position of the gantry. The identification of such errors is carried out by a correlation of the angular position of the gantry, indicated by the position of the X-ray tube fastened to the gantry, with the occurring errors. FIG. 5 shows a segment of the measured gantry position over a particular time interval in comparison with the chronological occurrence of errors within this time interval. FIG. 6 shows a histograms derived from this measurement that represents the number of errors dependent on the gantry position. If such a histogram shows a clear peak at a particular gantry position, as in the present example, this is an indication of an error of the transmission ring at this position.

Figure 7:
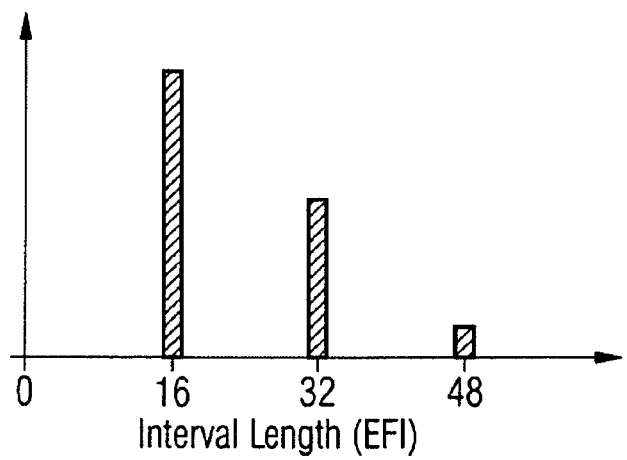
FIG. 7 is an example of a histogram of the distribution of the error-free intervals.
Figure 8:
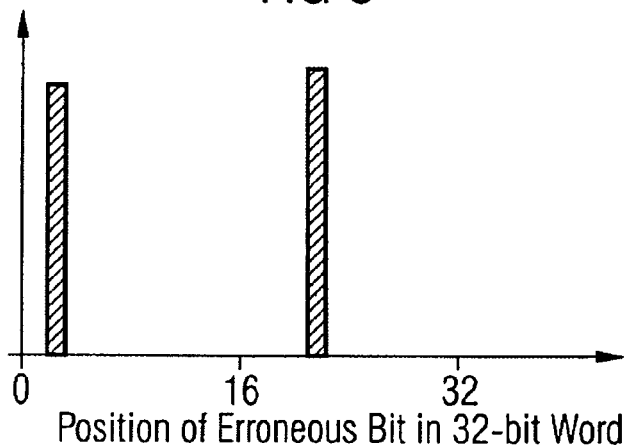
FIG. 8 is an example of a histogram showing the number of errors dependent on the error position inside a word.

FIGS. 7 and 8 show various histograms for the identification of errors caused by parallel/serial and serial/parallel converters or by parallel processors. For the identification of such errors, in the present example histograms are produced from the error data that indicate the distribution of the error-free interval length (FIG. 7), as well as the number of errors dependent on the position of the errors within a 32-bit word (FIG. 8). If peaks occur in the histograms at the intervals of the word length of data acquisition unit 1 (in the present example, 16 bits) or of the receiver of the image reconstruction unit 7 (32 bits in the present example), this is a concrete indication that the error is located in the corresponding component. FIG. 7 here gives an indication of an internal random bit error in the same bit within the 16-bit parallel bus. FIG. 8 gives an indication of an internal error at two bit positions within the 32-bit word.

Figure 9:
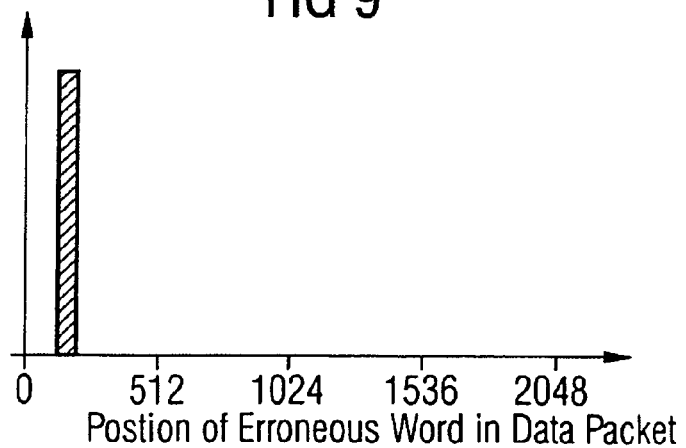
FIG. 9 is an example of a histogram showing the number of errors dependent on the position of the erroneous word inside a data packet.

FIG. 9 shows a further example of a histogram that indicates the number of errors dependent on the position of the data word within the transmitted data packet. Using his histograms, errors can be determined that occur in the parallel processing within a data packet. During the parallel processing, when errors occur only some words within a data packet are wrongly processed. If a peak occurs at a particular word position in the histograms, this indicates that the source of error is located in the parallel packet processor.

By the production of a packet having a repeating bit pattern by the bit pattern generator, errors can also be recognized that are caused by a particular bit combination, known as pattern-sensitive errors. Such errors can also be recognized by a histogram as shown in FIG. 9. As a rule, these errors are caused by errors in electronic circuits.

The present error analysis module also can determine the source of random bit errors that are caused by a poor signal-noise ratio or by errors due to external sources of interference. For this purpose, histograms of the distribution of the error burst length, as well as of the distribution of the error-free intervals, are produced, as can be seen in FIGS. 10 and 11. FIG. 10 shows histograms that indicate random bit errors. In this case, the error distribution is dominated by isolated bit errors, because the probability of two or more successive bit errors is very low. In addition, the histogram of the error-free interval length indicates a ramp-shaped distribution, which additionally indicates the randomness of the errors. When such random bit errors are detected, as a rule they are caused by a poor signal-noise ratio in a part of the transmission chain that transmits the low-level signal. For this reason, this can be an indication that the optical input signal of the optical receiver or the electrical signal level at the input of the RF receiver lies below tolerable boundary levels. This hypothesis can be additionally confirmed by the visual display units at the corresponding components, as shown in FIG. 2.

The histograms of FIG. 11 show an indication of the presence of an external source of the interference. In this case, the histograms of the distribution of the error burst length and of the error-free interval length indicate a random burst error distribution. Such random burst errors are an indication of a natural, external interference, for example due to other medical or non-medical devices operated in the vicinity of the computed tomography apparatus.

The present data transmission system provides an integrated error monitoring and diagnosis tool with which the quality of the data connection can be quantitatively acquired, even if the computed tomography apparatus is operated in normal operating mode, i.e., during standard patient exposures, without having to use additional test devices. By the use of an integrated error analysis module and the integrated bit pattern generator, the search for the errors can be carried out faster, more easily, and with reduced costs, in the clinical environment.

Although modifications and changes may be suggested by those skilled in the art, it is the intention of the inventor to embody within the patent warranted hereon all changes and modifications as reasonably and properly come within the scope of his contribution to the art.

I claim:

1. In a computed tomography device having a data acquisition unit in which measurement data are acquired and converted into a bit stream and communicated to a transmitter apparatus situated on a rotating part of the computed tomography device, the transmitter apparatus transmitting the bit stream to a stationary part of the computed tomography device, and having a receiver apparatus situated on the stationary part for receiving the bit stream from the transmitter apparatus and for communicating the bit stream to an image reconstruction unit for reconstructing an image from the bit stream, the improvement of a data transmission system comprising:

a first error recognition module disposed in said transmitter apparatus and a second error recognition module disposed in said receiver apparatus, each of said first and second error recognition modules monitoring said bit stream for errors and, upon detection of an error, generating an error signal; and an error processor in communication with said first and second error recognition modules and supplied with said signals therefrom for determining a quantity selected from the group consisting of an error number, an error rate and an error duration, and for storing said quantity in a log data file for evaluation.

2. The improvement of claim 1 wherein said bit stream contains CRC codes, and wherein each of said first and second error recognition modules comprises a module for monitoring said CRC codes.

3. The improvement of claim 1 wherein said bit stream has a signal level associated therewith, and wherein each of said first and second error recognition modules comprises a module for monitoring said signal level.

4. The improvement of claim 1 wherein said bit stream contains a clock signal, and wherein each of said first and second error recognition modules comprises a module for monitoring recoverability of said clock signal.

5. The improvement of claim 1 further comprising an error recognition module disposed in said image reconstruction unit.

6. The improvement of claim 1 comprising a bit pattern generator disposed in said data acquisition unit for, upon an entered command, producing an evaluatable bit pattern for conversion and transmission.

7. The improvement of claim 6 comprising an error analysis module in said image reconstruction unit for analyzing said quantity in said log data file in combination with said bit pattern from said data acquisition unit.

8. The improvement of claim 7 wherein said error analysis module determines a bit error rate for predicting a quality of a data connection proceeding from said data acquisition unit to said image reconstruction unit in a plurality of different operating modes of said computed tomography device.

9. The improvement of claim 8 wherein said error analysis module conducts an evaluation for identifying errors if said bit error rate exceeds a predetermined threshold value.

10. The improvement of claim 7 wherein said error analysis module detects systematic bit errors and burst errors.

11. The improvement of claim 7 wherein said error analysis module detects random bit errors and burst errors.

12. The improvement of claim 7 wherein said error analysis module detects at least one of position-related errors and pattern-sensitive errors.

13. The improvement of claim 1 wherein said error processor generates a warning message if said quantity exceeds a predetermined threshold.

14. The improvement of claim 1 comprising a first visual indicator connected to said first error recognition module for providing a visual indication if an error in said bit stream is recognized by said first error recognition module, and a second visual indicator connected to said second error recognition module for providing a visual indication if an error in said bit stream is detected by said second error recognition module.

15. The improvement of claim 14 wherein each of said first and second visual indicators comprises a light-emitting diode that is illuminated when said error in said bit stream is detected.

16. A method for monitoring data transmission in a computed tomography device wherein measurement data are acquired in a data transmission unit and are converted into a bit stream and communicated to a transmitter apparatus on a rotating part of the computed tomography apparatus, from which the bit stream is transmitted to a receiver apparatus situated on a stationary part of the computed tomography apparatus, and wherein said receiver apparatus communicates the bit stream to an image reconstruction unit for reconstructing an image from the bit stream, comprising the steps of:

in said transmitter apparatus and in said receiver apparatus, monitoring said bit stream in real time for errors; and storing a quantity associated with said errors selected from the group consisting of an error number, an error and an error duration, in a log file for evaluation.

17. A method as claimed in claim 16 wherein said bit stream contains CRC codes, and wherein the step of monitoring said bit stream for errors comprises monitoring said CRC codes.

18. A method as claimed in claim 16 wherein said bit stream has a signal level associated therewith, and wherein the step of monitoring said bit stream for errors comprises monitoring said signal level.

19. A method as claimed in claim 16 wherein said bit stream contains a clock signal, and wherein the step of monitoring said bit stream for errors comprises monitoring recoverability of said clock signal.

20. A method as claimed in claim 16 comprising also monitoring said bit stream for errors in said image reconstruction unit.

21. A method as claimed in claim 16 wherein, upon an entered command, generating a predetermined bit pattern in said data acquisition unit and converting said bit pattern into said bit stream, and transmitting said bit stream.

22. A method as claimed in claim 21 comprising analyzing said bit pattern in said bit stream for errors in said image reconstruction unit.

23. A method as claimed in claim 16 comprising, from said quantity stored in said log data file, generating a quantitative prediction of a quality of a data connection proceeding from data acquisition unit to said image reconstruction unit in a plurality of different operating modes of said computed tomography device.

24. A method as claimed in claim 23 comprising, if a threshold value for said bit error rate is exceeded, generating a histogram representing a distribution of lengths of error bursts and a distribution of lengths of error-free intervals.

25. A method as claimed in claim 23 comprising, if a threshold value for said bit error rate is exceeded, generating a histogram representing a number of errors dependent on an associated position of said rotating part.

26. A method as claimed in claim 23 comprising, if a threshold value for said bit error rate is exceeded, generating a histogram representing a number of errors dependent on the bit position within transmitted bit words.

27. A method as claimed in claim 23 comprising, if a threshold value for said bit error rate is exceeded, generating a histogram representing a number of errors dependent on a position of an erroneous word within transmitted data packets.

28. A method as claimed in claim 16 comprising, if a predetermined threshold value for said quantity is exceeded, generating a warning message.

* * * * *